United States Patent [19]

Hayes et al.

[11] Patent Number: 5,052,802
[45] Date of Patent: Oct. 1, 1991

[54] DEVICE FOR VIEWING BENEATH CIRCUIT BOARDS

[75] Inventors: James M. Hayes; Kevin L. Wible; Robert L. Kelley, all of Loveland, Colo.

[73] Assignee: Hewlett-Packard Company, Palo Alto, Calif.

[21] Appl. No.: 557,251

[22] Filed: Jul. 24, 1990

[51] Int. Cl.⁵ .................... G01N 21/88; G02B 23/24
[52] U.S. Cl. .................................. 356/237; 356/241; 359/798; 359/802; 359/726; 359/882
[58] Field of Search ................ 356/241, 237; 350/235, 350/243, 244, 506, 640

[56] References Cited

U.S. PATENT DOCUMENTS 1,292,326  1/1919  Jacobson .................. 350/235 X
2,725,788  12/1955 Pfleger ...................... 350/235
3,481,660  12/1969 Sheldon ................... 356/241 X
4,938,579   7/1990 Kempf ...................... 350/640

OTHER PUBLICATIONS

Johnson et al "Optical System for Viewing Dielectric Smear in Printed Circuit Board Hole and Deleting the Smear" IBM Tech. Disc. Bulletin, vol. 25 #9, Feb. 1983, pp. 4513-4514.

Primary Examiner—Vincent P. McGraw

[57] ABSTRACT

A hand-held, portable, visual inspection aid is described which has a variety of uses in diverse fields, e.g., manufacturing, service and repair industries, health care field, hobby field, etc. The inspection aid includes a light source and a prism having one mirrored surface. Optionally there may also be included a magnifying lens for magnifying the image viewed through the prism. The device is useful for visually inspecting objects in areas not readily viewed with the naked eye.

15 Claims, 4 Drawing Sheets

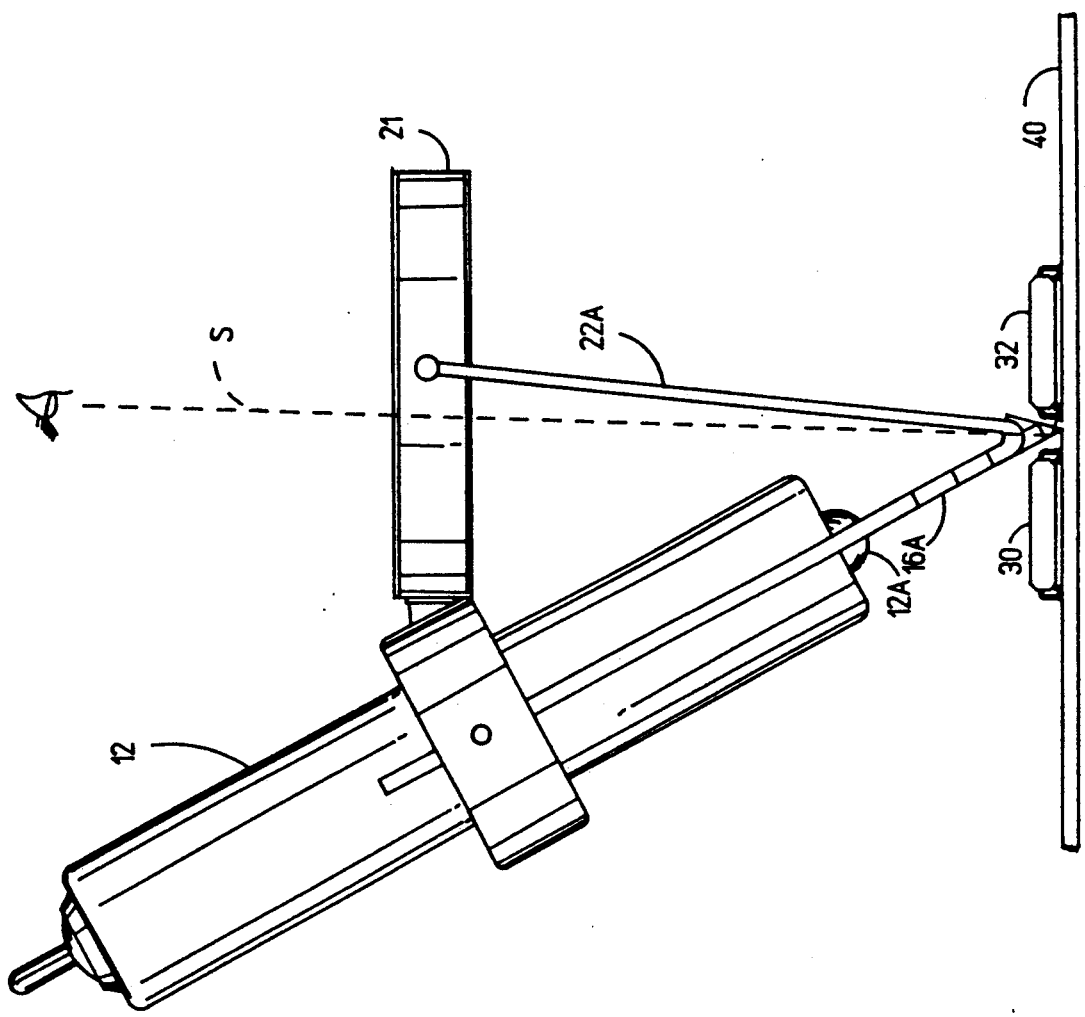

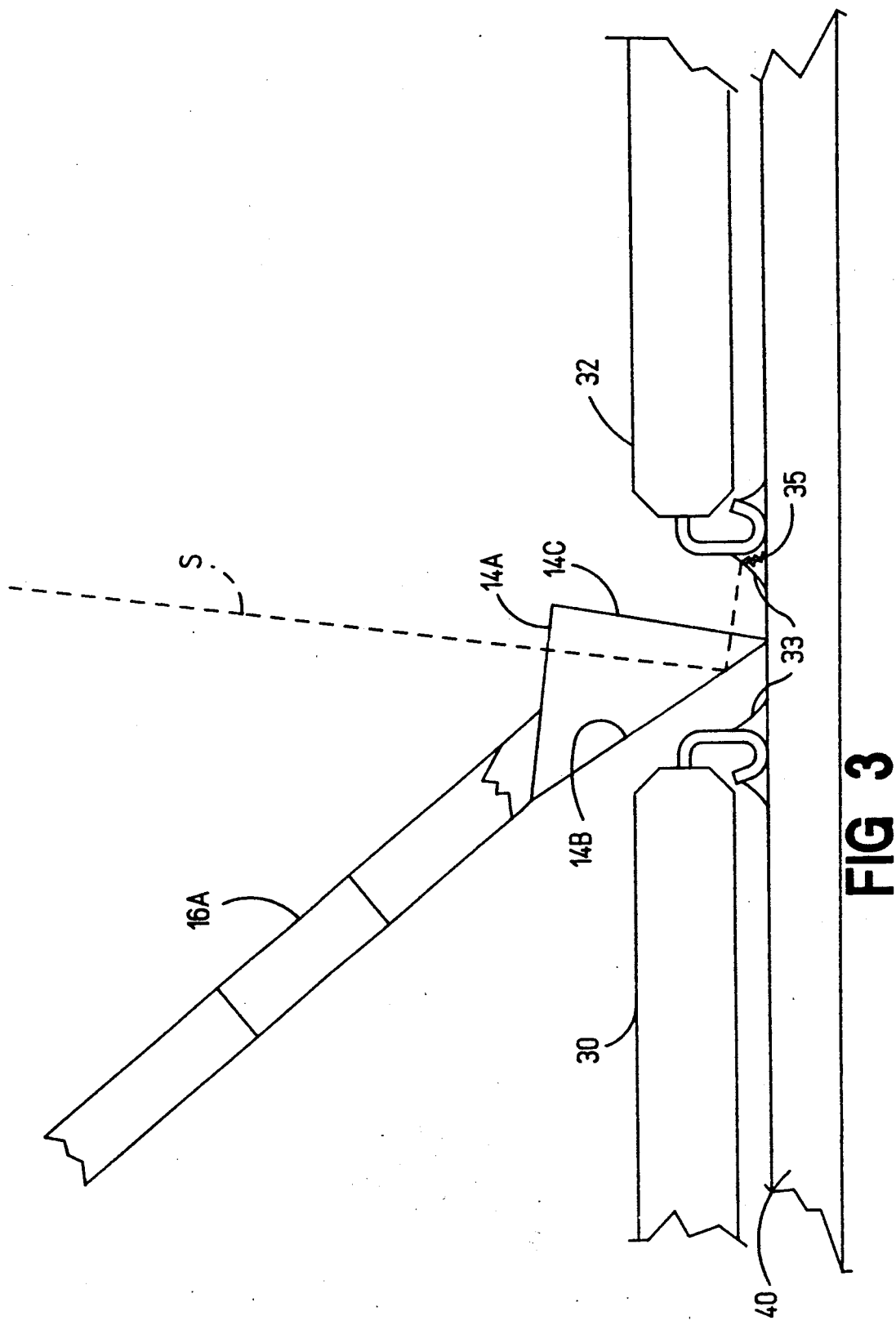

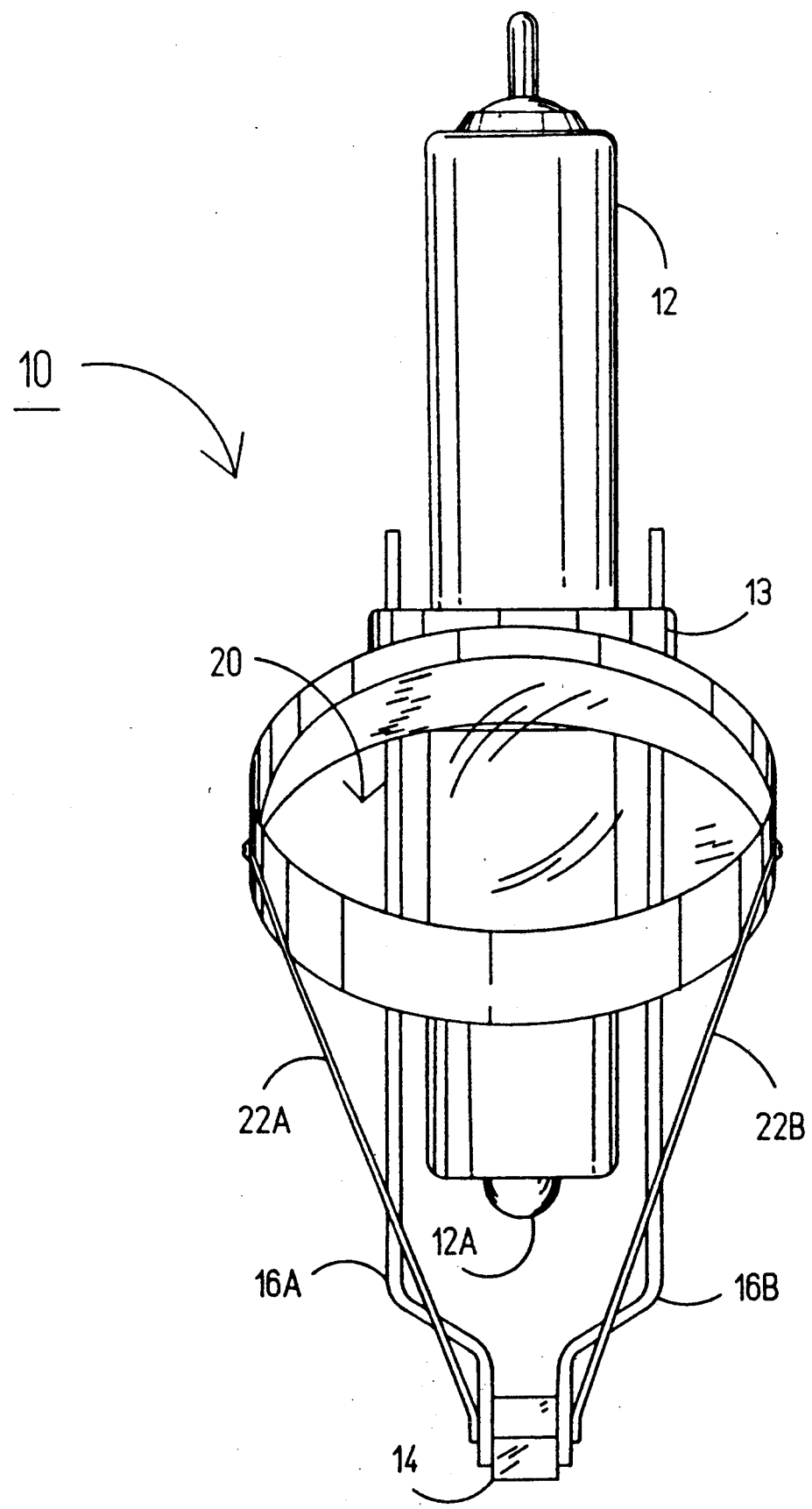

DEVICE FOR VIEWING BENEATH CIRCUIT BOARDS

FIELD OF THE INVENTION

This invention relates to inspection aids. More particularly, this invention relates to visual inspection aids and devices. In another aspect, this invention relates to visual inspection aids for use in connection with the manufacture and testing of printed circuit boards or the like.

BACKGROUND OF THE INVENTION

In conventional printed circuit boards manufactured currently there are typically numerous electronic components secured to a dielectric or insulating substrate. Each electronic component typically includes a plurality of leads which must be soldered to conductive pads carried on the dielectric substrate.

Current technology for mounting electronic devices or components on printed circuit boards is commonly referred to as surface mount technology. In this technique the components are mounted to solder pads on one or both faces of the printed circuit board. Such technology allows higher density packing of electronic components on a circuit board than is possible using other mounting technology such as through-hole lead mounting.

The types of leads on integrated circuit chips which are commonly used in surface mounting are J-leads and gull wing leads. These types of leads extend downwardly from the side or underside of the electronic component and are simply soldered to a connection pad on the same side of the board on which the electronic component is mounted. Use of the J-leads is especially advantageous because they require less space than other types of leads by reason of the fact that the solder pad is physically located beneath the component. However, gull wing leads are easier to inspect and repair.

Unfortunately, the higher density packing of electronic components on a printed circuit board renders it difficult to adequately inspect the quality of solder joints or bonds between the leads of the electronic component and the pad on the printed circuit board. Because of the very close spacing of the electronic components, it is difficult to visually inspect under or between the components to determine whether all leads have been soldered, or whether any solder fillets or joints have cracked or failed.

Although printed circuit boards can be tested electronically to determine whether there are any defects, this is time consuming, expensive, and not totally accurate. Furthermore, it is still necessary to inspect or test individual fillets or joints to verify that proper electrical connections have been made.

It is possible to inspect J-lead connections by tilting the printed circuit board on edge and then visually examining the connections using a large microscope. However, this is a an awkward and very tedious procedure, and some solder joints are visually obscured by adjacent tall components. Also, many incorrect or defective J-lead solder joints cannot be visually observed from directly above a component on the board.

By increasing the spacing between electronic components on the printed circuit board it is easier to visually inspect the connections. However, this defeats the purpose of using J-leads to allow close spacing of components.

There has not heretofore been provided a hand-held, portable, visual inspection aid which is suitable for inspecting connections on printed circuit boards where electronic components are closely spaced.

SUMMARY OF THE INVENTION

In accordance with the present invention there is provided a hand-held, portable, visual inspection aid which can be used in a variety of applications where it is difficult or impossible to see with the naked eye.

In one embodiment the inspection aid device comprises:

(a) a light source for emitting a light beam; and
(b) a prism suspended from the light source in the light beam.

The prism includes a mirror on one surface to reflect light through and away from the prism onto the object to be viewed.

In another embodiment there may be included a magnifying lens for viewing the image through the prism. The position of the magnifying lens may be varied relative to the prism, as desired.

Although the visual inspection aid of this invention has primary utility in the inspection of solder fillets or joints in printed circuit boards, it also has utility in many other fields. For example, it may be used in medical applications, dentistry, small appliance examination, hobby field, etc. The inspection aid can be used anywhere where it is necessary to visually inspect an object and it is not possible or practical to do with the naked eye.

Use of the inspection aid of the invention is simple and efficient. It is also an inexpensive aid which is effective in viewing into small areas or around corners, under components, etc..

The inspection aid is easy to manufacture and it is small and compact. It is also easy to adjust the position of the prism relative to the light source and magnifying lens (if present). Because of its small size, the prism can be slipped between tall components to reach into areas which are otherwise not accessible. Also, because the inspection device includes its own source of light, it provides its own required illumination. No expensive or complex support equipment is required. The prism directs the light precisely where it is needed and it is more compact than a conventional mirror.

Other advantages of the inspection aid of the invention will be apparent from the following detailed description.

BRIEF DESCRIPTION OF THE DRAWINGS

The invention is described in more detail hereinafter with reference to the accompanying drawings, wherein like reference characters refer to the same parts throughout the several views and in which:

FIG. 2 is a side elevational view of the embodiment of FIG. 1 being used to inspect solder fillets or joints on a printed circuit board;

FIG. 3 is a partial cutaway side elevational view illustrating the use of the inspection aid; and FIG. 4 is a front elevational view of one embodiment of inspection aid of the invention.

DETAILED DESCRIPTION OF THE INVENTION

Figure 1:
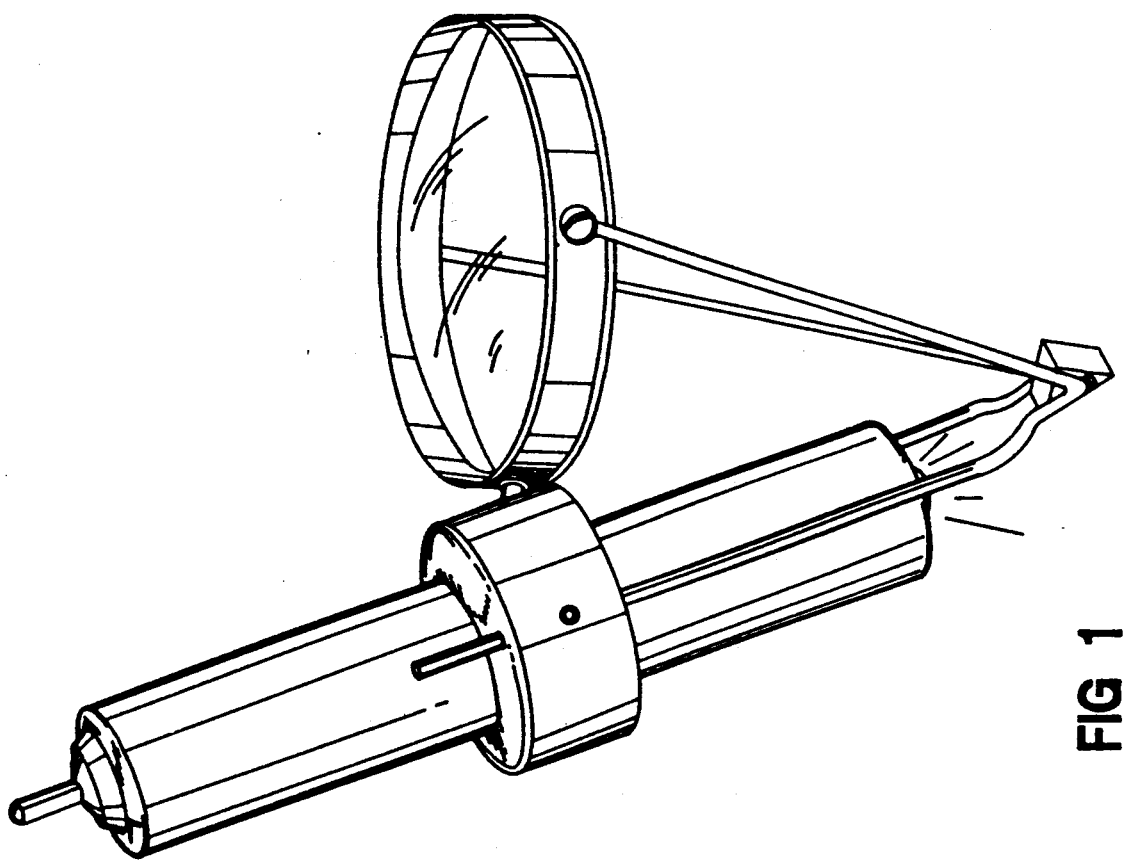
FIG. 1 is an isometric view of one embodiment of visual inspection aid of the invention.

In the drawings there is illustrated one embodiment of a visual inspection aid 10 of the invention which is particularly useful in the visual inspection of printed circuit boards, e.g., to determine whether all of the leads of electronic components on the board have been properly soldered to the appropriate connection pads on the board. As more and more electronic components are mounted on printed circuit boards, the density of such components on the board increases. This makes it very difficult to visually inspect each solder joint or fillet to determine whether it has been properly made or whether it has been damaged. The inspection aid described herein enables such solder joints or fillets to be visually examined very easily and efficiently.

The visual inspection aid 10 comprises a light or illumination source including housing 12, bulb 12A, actuation switch 12B, and batteries within the housing for providing the electrical energy required to power the bulb when desired. A prism 14 is suspended below the bulb 12A by means of support legs 16A and 16B in a manner such that the prism is within the beam of light emitted by the bulb 12A. There may be one or more such support legs 16A and 16B. Preferably such support legs are attached to the sides of the prism, as illustrated.

Optionally, there may be included a magnifying lens 20 which is carried by the light source and held in position above the prism in a manner such that the prism is viewed through the magnifying lens, whereupon the viewed image is magnified for easier viewing. The magnifying lens may include a frame 21 which may be pivotably and adjustably attached by means of pin 24 to collar 13 on housing 12. Support legs 22A and 22B extend between the frame 21 and the prism (or the lower end of legs 16A and 16B). Alternatively, legs 22A and 22B may be integral with legs 16A and 16B, respectively. The upper ends of legs 22A and 22B are attached to the frame 21 (e.g., by means of a screw 23).

The prism may be suspended below the bulb 12A any desired distance. Normally the prism is suspended below the bulb at a distance in the range of about 0.5 to 2 inches, depending upon the height of the components it must reach between, the desired angle of view, the intensity of the light source, and the extent to which the light beam is collimated before reaching the prism. The bulb 12A may include an integral lens for collimation of the light. As another alternative, a reflector may be included to collimate the light. The bulb is conveniently powered by batteries (e.g., AA size).

The size of the prism may also vary. Typically the width of the prism is in the range of about 0.2 to 0.5 inch. The height of the prism may also vary in the same range.

Preferably the prism has a triangular cross-section as illustrated in the drawings. The back surface 14B of the prism is a mirror and it preferably is oriented at an angle of 45° relative to the top surface 14A and also the front surface 14C. The lower edge of the prism may be a relatively sharp edge or it may be a small polished radius.

As illustrated in FIGS. 2 and 3, the line of sight S is perpendicular to the top surface 14A of the prism. In this manner the light is reflected off the shiny back mirror surface 14B of the prism so that the light is perpendicular to the top face 14A and also the front face 14C of the prism. In this manner the light is not distorted while passing through the prism. Accordingly, the image viewed through the prism is not distorted.

In order to visually inspect solder joints or fillets beneath, or adjacent to, electronic components on a printed circuit board, the device 10 is held such that the prism 14 is positioned in the space between adjacent electronic components 30 and 32 on board 40. This is illustrated in FIGS. 2 and 3.

The pointed or narrow lower edge of the prism easily fits into the narrow gap or space between adjacent electronic components. As a result, it is possible to visually inspect between adjacent electronic components on the board (one side at a time) to detect a crack or defect 35 in a solder fillet 33, for example. It is also possible to visually inspect under some electronic components. Also, when using a small prism, only a few joints are observed at one time, thereby allowing more concentration on each joint by the viewer.

Thus, the device of the invention is extremely useful in visually inspecting the quality and adequacy of solder joints or fillets 33 between leads of electronic components and the pads to which such leads are bonded. The device of the invention enables quick and efficient inspection of the fillets or bonds on a printed circuit board.

The magnifying glass or lens 20 optionally provided on the device 10 provides for magnification of the visual image observed through the prism. The size and magnification of the lens 20 may vary, as desired. For example, and not by way of limitation, the lens may be 1 to 3 inches in diameter and have a magnification of 2 to 5×X. Of course, higher magnifications are also possible.

Preferably the lens is aligned in a plane parallel to the top face 14A of the prism, although tilting of the lens relative to the prism may be desired at times. Also, the lens may be folded up against the housing 12 for transport or storage, if desired. The lens may also be detachable, if desired.

It is also preferable for the lens to be positioned such that the focal point is at the surface of the mirror plane 14B. As another alternative, a convex lens could be positioned directly on top of face 14A of the prism. This would be a more compact design.

Other variants are possible without departing from the scope of the present invention.

What is claimed is:

1. A hand-held, portable, visual inspection aid comprising:
    (a) a light source for emitting a light beam; wherein said light source comprises an elongated housing having upper and lower ends and a bulb carried at said lower end for emitting said beam; wherein said light source further includes actuation means for turning said light beam on and off; and
    (b) a prism suspended from said light source in said light beam below said lower end;
   wherein said prism includes a mirror; and wherein said prism includes two faces which are perpendicular to each other, and wherein said mirror extends between said two faces at an angle such that light entering said prism through one said face is reflected by said mirror through the other said face.

2. An inspection aid in accordance with claim 1, wherein said two faces are of equal size, and wherein said mirror extends between said two faces at an angle of approximately 45° with respect to each said face.

3. An inspection aid in accordance with claim 1, further including first and second support legs each having first and second ends, wherein said first end of each said support leg is secured to said housing, and wherein said prism is secured between said second ends of said support lets.

4. An inspection aid in accordance with claim 1, further comprising a magnifying lens above said prism; wherein said lens is supported by said housing, and wherein the position of said magnifying lens relative to said prism is adjustable.

5. An inspection aid in accordance with claim 3, wherein the position of said prism relative to said light source is adjustable.

6. An inspection aid in accordance with claim 3, further comprising a magnifying lens above said prism, wherein said lens is carried by said housing, and further comprising support arms extending between said lens and said prism.

7. A method for visually inspecting an object comprising:
   (a) providing a hand-held, portable device comprising:
      (i) a light source for emitting a light beam; wherein said light source comprises an elognated housing having upper and lower ends and a bulb carried at said lower end for emitting said beam; wherein said light source further includes actuation means for turning said light beam on and off; and
      (ii) a prism suspended from said light source in said light beam below said lower end; wherein said prism includes a mirror for reflecting light out of said prism wherein said prism includes two faces which are perpendicular to each other, and wherein said mirror extends between said two faces at an angle such that light entering said prism through one said face is reflected by said mirror through the other said face;
   (b) positioning said prism adjacent said object to be inspected; and
   (c) viewing said object through said prism.

8. A method in accordance with claim 7, wherein said object comprises an electronic component.

9. A method in accordance with claim 8, wherein said electronic component is carried on a printed circuit board; wherein said electronic component includes leads which are soldered to said printed circuit board; and wherein said leads can be visually inspected through said prism.

10. A method in accordance with claim 7, wherein said device further comprises a magnifying lens supported by said light source above said prism; wherein the position of said magnifying lens relative to said prism is adjustable.

11. A method in accordance with claim 9, wherein said leads comprise J-leads.

12. A method in accordance with claim 9, wherein said electronic component includes an underside, and wherein said leads extend downwardly from said underside.

13. A method in accordance with claim 9, wherein there are a plurality of said electronic components carried on said printed circuit board; wherein at least one gap is defined between adjacent electronic components; and wherein said prism can be positioned in said gap to thereby visually inspect said leads.

14. A method in accordance with claim 13, wherein said leads comprise J-leads.

15. A method in accordance with claim 13, wherein each said electronic component includes an underside, and wherein said leads extend downwardly from said underside.

* * * * *